United States Patent
Avalle

(10) Patent No.: US 6,372,232 B1
(45) Date of Patent: Apr. 16, 2002

(54) PROCESS FOR THE PREPARATION OF COSMETIC PRODUCTS THROUGH THE USE OF CO2

(75) Inventor: Nadia Avalle, Milan (IT)

(73) Assignee: Intercos Italia S.p.A., Milan (IT)

( * ) Notice: Subject to any disclaimer, the term of this patent is extended or adjusted under 35 U.S.C. 154(b) by 0 days.

(21) Appl. No.: 09/541,907

(22) Filed: Apr. 3, 2000

(30) Foreign Application Priority Data

May 20, 1999 (IT) .......................................... MI99A1107

(51) Int. Cl.$^7$ ................................................. A61K 7/00
(52) U.S. Cl. ......................................................
(52) U.S. Cl. ........................................ 424/401; 424/69
(58) Field of Search .................................. 424/401, 69

(56) References Cited

PUBLICATIONS

Patents Abstracts of Japan, vol. 1999, No. 5, May 31, 1999 & JP 11 047681 A (Kira Keshohin), Feb. 23, 1999.*

Richard J. Lewis, Sr. Condensed Chemical Dictionary (1997), John Wiley & Sons, Inc., 13th Edition, p. 898.*

Patent Abstracts of Japan, vol. 1999, No. 5, May 31, 1999 & JP 11 047681 A (Kira Keshonin), Feb. 23, 1999.

* cited by examiner

Primary Examiner—Jose G. Dees
Assistant Examiner—Konata M. George
(74) Attorney, Agent, or Firm—Jacobson Holman, PLLC

(57) ABSTRACT

There is described a process for the-preparation of cosmetic products, in particular cosmetic products. The process comprises the preparation of 5–99.999% by weight of a powder phase, the preparation of 0.0001–95% by weight of an oily, waxy and/or polymeric lipid phase and the mixture of the two phases through the use of CO2 as a solvent, in supercritical condition and non.

9 Claims, No Drawings

PROCESS FOR THE PREPARATION OF COSMETIC PRODUCTS THROUGH THE USE OF CO2

DESCRIPTION

The present invention concerns a process for the preparation of cosmetic products, in particular of coated powders utilised in makeup cosmetic products or of finished cosmetic products, through the use of $CO_2$ in supercritical conditions and non.

As a coating phase for a powder an oily, waxy or polymeric lipid phase is herein meant that is soluble or dispersable in $CO_2$, even by addition, if required, of a co-solvent as water, toluene, benzene, methanol, acetone, chloroform, ammonia, etc.

The mixing of a powder phase with an oily, waxy or polymeric lipid phase is one of the most common operations for the obtainment of a cosmetic product. This operation can have as an object to "ennoble" the powder in order to enhance its characteristics or to obtain a simple mixture of the two phases. This operation is generally carried out in mills of various kind, where the two phases are mixed for a variable time (sometimes very long) until the obtainment of a homogeneous product.

This technology however leaves unresolved some defect problems as for instance:
  the difficulty in obtaining a homogeneous mixture in presence of an oily, waxy or polymeric lipid phase, with quanity lower than 3% by weight;
  problems with breaking of precious and fragile ingredients (for instance pearls) as a consequence of an excessive machining;
  difficulty in correcting the colour of a powder mixture previously mixed to an oily, waxy or polymeric lipid phase.

The difficulty in obtaining a homogeneous mixture in products where the oily, waxy or polymeric lipid phase is present in quantity lower than 3% by weight can be partly overcome by diluting the non powder phase in a proper solvent before being atomised on the dry phase. This operation can be carried out in continuous or discontinuous turbine mixing systems (batch). Once mixed, the product must be dried in order to remove the excess solvent. This technique leads to the formation of agglomerates and in any case does not solve the problem of the correction of the colour once the mixture has been done.

This latter problem can be solved by using a very large quantity of solvent in order to carry out the mixture in the slurry phase. This operation must be carried out every time the colour has to be modified.

At this point the choice of the solvent is very important and it must possibly meet these characteristics:
  Harmless for man and for the environment;
  low boiling (in order to be easily removed without excessive expenditure of energy);
  good solvent power for the substances that are wanted to be mixed;
  it must not be inflammable;
  it must have a relatively low cost.

The solvents commonly used by the chemical industry hardly meet these requirements.

In view of this state of the art, object of the present invention is to realise a process for the preparation of cosmetic products, particularly cosmetic products for makeup in the form of coated powders or of finished. cosmetic products, that are capable to resolve the aforesaid problems.

An additional object is to realise a process that allows to prepare a mixture of the powder phase and the oily, waxy or polymeric lipid phase with a concentration varying from 0.1% to 95% by weight preferably between 1% by weight and 50% by weight in a latter phase.

The objects of the invention are attained owing to a process comprising:
  a) the preparation of 5–99.999% by weight of a powder phase;
  b) the preparation of 0.0001–95% by weight of an oily, waxy and/or polymeric lipid phase;
  c) the mixture of the two phases through the use of a solvent;
  characterized in that it uses the $CO_2$ as a solvent.

It was possible to observe that the $CO_2$, in supercritical conditions and non, meets all the requirement required of a solvent for the obtainment of a homogeneous mixture of the two component phases.

The powder phase can be made up of various excipients traditionally used in cosmetics, as talc, mica, kaolin, starch, oxide of zinc, nylon 12, polyethylene, silica, spherical silica, acrylate polymers and co-polymers, etceteras, alone or in mixture among them or in combination with pigment as iron oxides, chromium oxides, chromium hydroxides, ultramarine blue, ultramarine pink, manganese violet, titanium dioxide, mica base pearls and titanium dioxide, mica base pearls and bismuth oxychloride, carmine, lakes and organic dye base pigment as by CTFA.

By oily, waxy or polymeric lipid phase it is meant: oils, waxes, surfactants, silicones, perfluorides, other non coated or otherwise coated powders, perfumes and other more.

EXAMPLE 1

A powder mixture of talc, Nylon, pearls and Stearate Zn (860 g) and a liquid mixture of Eutanol G, Satoil Ceraphil 847 and Akam (140 g) have been mixed for 60' in a small bench reactor (2.4 dmc) with magnetic drive (anchor blade with speed of 30 rpm) saturated with $CO_2$ at the pressure of 100 bar and at the temperature of 50° C. Once the mixing has been completed the product has been unloaded sieved and compacted.

EXAMPLE 2

As the previous trial but with the powder phase of 850 g and liquid phase of 150 g. In this case a blades agitator has been used.

EXAMPLE 3

As example 1 with pressure at 150 bar, temperature at 60° C. and agitation 350 rpm.

EXAMPLE 4

A mixture of talc, mica, preservatives, pearls and colours powder phase (650 g) and a phase of PEG 60, Vaseline oil, Trialan 308, silicone 200/100, fluid 556, Cosmol 525, Arlacel 60, Glucam E-20, Rheopearl KL and Anoxid BHT (350 g) has been mixed in a small bench reactor saturated with $CO_2$ for 90' at the speed of 300 rpm, P=120 bar and T=50° C. Once the mixture has been carried out the product has been sieved and compacted.

EXAMPLE 5

A mixture of talc, mica, preservatives, pearls, colours, nylon, silica and polymethylmetacrylate powder phase (700 g) and a phase of PEG 60, oil of Vaseline, Trialan 308, silicone 200/100, fluid 556, Cosmol 525, Arlacel 60, Glucam E-20, Rheopearl KL and Anoxid BHT (300 g) has been mixed in a small bench reactor saturated with CO2 for 90' at the speed of 300 rpm, P=120 bar and T=50° C. Once the mixing has been completed the product has been sieved and drawn.

What is claimed is:

1. A process for preparing a cosmetic product, comprising mixing a powder phase and an oily phase, a waxy phase, a polymeric lipid phase, or a combination thereof, together by using a solvent comprising $CO_2$ in a non-supercritical condition.

2. The process of claim 1, wherein the cosmetic product is suitable for use as makeup and is in the form of a coated powder or a finished cosmetic product.

3. The process of claim 1, wherein the powder phase is from 5% to 99.999% by weight and the oily phase, the waxy phase, or the polymeric lipid phase is from 0.0001% to 95% by weight.

4. The process of claim 1, wherein the two phases are mixed directly, without pre-machining.

5. A mixture of powders and oils, waxes, polymers, or a combination thereof, comprising a powder phase and an oily phase, a waxy phase, a polymeric lipid phase, or a combination thereof, wherein the phases of the mixture were mixed together with a solvent comprising $CO_2$ in a non-supercritical condition.

6. The mixture of claim 5, wherein the powder phase is from 5% to 99.999% by weight and the oily phase, the waxy phase, or the polymeric lipid phase is from 0.0001% to 95% by weight.

7. A cosmetic composition comprising a powder phase and at least one cosmetically acceptable component, wherein the powder phase and the cosmetically acceptable component were mixed together with a solvent comprising $CO_2$ in a non-supercritical condition.

8. The cosmetic composition of claim 7, wherein the powder phase is from 5% to 99.9% by weight and the cosmetically acceptable component is from 1% to 95% by weight.

9. The cosmetic composition of claim 7, wherein the cosmetically acceptable component is an oil, a wax, a polymeric lipid, or a combination thereof.

* * * * *